United States Patent [19]

Davister et al.

[11] Patent Number: 5,733,560
[45] Date of Patent: Mar. 31, 1998

[54] METHOD OF IMPROVING RETENTION TIME OF VOLATILE ORGANIC CHEMICAL COATED ON A SURFACE

[75] Inventors: Michele Davister, Vise; Guy Broze, Grace-Hollogene; Patrick Durbut, Verviers; Hoai-Chau Cao, Liege, all of Belgium; Thomas Connors, Piscataway, N.J.; John Labows, Horsham, Pa.; Anne-Marie Misselyn, Villers-l'eveque, Belgium

[73] Assignee: Colgate-Palmolive Company, Piscataway, N.J.

[21] Appl. No.: 764,290

[22] Filed: Dec. 12, 1996

[51] Int. Cl.$^6$ .................................. A01N 25/24
[52] U.S. Cl. ................ 424/407; 512/2; 514/625; 510/422; 424/59
[58] Field of Search ................ 424/407; 512/2

[56] References Cited

FOREIGN PATENT DOCUMENTS 672747    9/1995    European Pat. Off. .

*Primary Examiner*—Bernard Dentz
*Attorney, Agent, or Firm*—Richard E. Nanfeldt; James M. Serafino

[57] ABSTRACT

A composition comprising: an organic chemical Which has a chemical group having a dipole moment of at least about 1.5 and a chemical linker composition which is an ethoxylated glycerol type compound and, optionally, a compound selected from the group consisting of carboxylic acids having 4 to 6 carbon atoms, a polyvinyl pyrrolidone and a polyethylene glycol having a molecular weight of about 600 to about 10,000, wherein the molar ratio of organic chemical to the chemical linker composition is about 4:1 to 1:4.

6 Claims, No Drawings

METHOD OF IMPROVING RETENTION TIME OF VOLATILE ORGANIC CHEMICAL COATED ON A SURFACE

FIELD OF THE INVENTION

The present invention relates to a method for improving the retention time of an additive coated on a surface which comprises adding chemical linkers to an organic chemical such as a perfume, insect repellent, antibacterial agent, and/or an allergen agent in order to reduce the rate of vaporization of the organic chemical from the surface to which it has been applied.

BACKGROUND OF THE INVENTION

A major problem is how long an organic chemical such as a perfume, fabric softener, sunscreen agent, insect repellent, antibacterial agent and/or allergen agent will be effective on a surface on which the organic chemical has been deposited. For example, if the lasting effect of a perfume deposited on the human skin could be increased the necessity for repeat application of the perfume would be reduced. Alternatively, if the concentration of the perfume in a solution could be reduced while maintaining its effectiveness substantial cost savings could be achieved. The present invention relates to chemical linkers which can be added to the organic chemical whereby the chemical linker by chemical association links the organic chemical to the surface on which the organic chemical has been deposited thereby decreasing the rate of vaporization of organic chemical. The requirement of the chemical linker is that when the chemical linker is added to an organic chemical that an exothermic interaction occurs between the chemical linker and the organic chemical which causes a reduction in the active vapor pressure of the organic chemical.

For example, Methylneodecanamide (MNDA) is an insect repellent agent which can be applied to a surface. This is necessary to deposit 10 micrograms of MNDA per cm2 to have one day efficacy. It is more than 500 molecular layers. To deliver this amount requires almost neat usage. Unfortunately, one may not increase the MNDA concentration. It is desirable to increase the repellency duration without increase MNDA quantity.

On the other hand, it would be desirable to have more formulation flexibility with high oil uptake capacity perfumes. The increase of the substantivity of these perfumes ingredients would make possible to either increase performance of the perfume, or deliver the same cleaning and olfacting results with less perfume. This invention teaches that chemical linkers are a way to deliver more efficiently organic chemicals such as MNDA or perfumes to a surface to which it has been applied.

SUMMARY OF THE INVENTION

The present invention relates to a process for improving the retention time of an organic chemical on a surface and to chemical compositions which comprise approximately by weight a complex of:

(a) an organic chemical having a chemical group with a dipole moment of at least about 1.5 selected from the group consisting of a chemical compound containing an amide linkage such as an insect repellents, antibacterial agents containing a carbon-halogen bond such as triclosan, allergen agents, fabric softener or sunscreen agent containing an ester group or enzymes containing acid groups and a chemical compound containing an aldehyde group or alcohol group such as those type of compounds present in perfumes and mixtures thereof; and (b) a chemical linker composition which undergoes an exothermic reaction with the organic chemical, wherein the chemical linker composition which is an ethoxylated glycerol type compound and, optionally, a compound selected from the group consisting of a polyvinyl pyrrolidone polymer and a carboxylic acid having about 4 to about 6 carbon atoms and a polyethylene glycol having a molecular weight of about 600 to about 10,000, preferably about 1,000 to about 8,000 wherein the ratio of chemical additive to chemical linker composition is about 4:1 to about 1:4.

The instant compositions excluded the use of ethoxylated nonionic surfactants formed for the condensation product of primary or secondary alkanols and ethylene oxide or propylene oxides because the use of these ethoxylated nonionic would cause a weakening of the chemical association between the chemical linker and the organic chemical surfactant.

The complex of the organic chemical and chemical linker compositioncan be applied neat to the surface which is being treated, wherein the chemical linker functions to bind the organic chemical to the treated surface. This invention relates to a method for improving the retention time of an organic chemical which comprises the step of adding said organic chemical having a chemical group having a dipole moment of at least about 1.5 on a surface to a chemical linker composition which is an ethoxylated glycerol type compound and a compound selected from the group consisting of carboxylic acids having 4 to 6 carbon atoms, a polyvinyl pyrrolidone polymer and a polyethylene glycol having a molecular weight of about 600 to about 10,000, wherein the molar ratio of the chemical linker composition to the organic chemical is about 4:1 to 1:4. Alternatively, the complex of the organic chemical and the chemical linker composition can be dissolved at a concentration of about 0.1 wt. % to about 99.9 wt. % in a solvent which dissolves both the chemical linker composition and the organic chemical. Alternatively, the complex of the chemical linker composition and the organic chemical can be incorporated into a cleaning composition such as a body cleansing formulation, a fabric softening composition, a body lotion, a shampoo, an oral cleaning composition, a light duty liquid composition, an all purpose or microemulsion hard surface cleaning composition and a fabric care cleaning composition.

The instant invention also relates to complexes of a chemical linker composition, an organic chemical having a dipole moment of at least about 1.5 and an anionic sulfonate, carboxylate or sulfate containing surfactant which can be optionally mixed with a surfactant selected from the group consisting of zwittionic surfactant, an amine oxide or an alkylene carbonate and mixtures thereof.

DETAILED DESCRIPTION OF THE INVENTION

The present invention relates to a complex comprising:

(a) an organic chemical having a chemical group having a dipole moment of at least about 1.5, more preferably at least about 1.6; and (b) a chemical linker composition which comprises an ethoxylated glycerol type compound and, optionally a compound selected from the group consisting of carboxylic acids having 4 to 6 carbon atoms, polyethylene glycols having a molecular weight of about 600 to about 10,000, and a polyvinyl pyrrolidone, wherein the mole ratio of chemical additive to chemical linker composition is about 4:1 to about 1:4. The present invention also relates to a solution of 0.25 wt. % to 99.75 wt. % of the complex of the organic chemical and chemical linker composition in a solvent which can solubilize the complex of the organic chemical and chemical linker composition.

The present invention further relates to a composition which comprises:

(a) 0.1 to 10 wt. % of an organic chemical having a chemical group with dipole moment of at least about 1.5, more preferably at least about 1.6;

(b) 0 to 30 wt. % of at least one anionic surfactant having a carboxylate, sulfate or sulfonate group;

(c) 0.1 to 30 wt. % of a chemical linker composition which is an ethoxylated glycerol type compound and, optionally, a compound selected from the group consisting of a polyvinyl pyrrolidone polymer, a polyethylene glycol having a molecular weight of about 600 to 10,000 and a carboxylic acid having 4 to 6 carbon atoms and mixtures thereof, wherein the chemical linker composition complexes both with the anionic surfactant and the organic chemical;

(d) 0 to 15 wt. % of an amine oxide surfactant, a zwitterionic surfactant and an alkylene carbonate surfactant and mixtures thereof, wherein the anionic surfactant complexes with the amine oxide, zwitterionic surfactant or alkylene carbonate; and (e) 15 to 99.8 wt. % of water.

The compositions of the instant invention can be in the form of a solution, a microemulsion, a gel or a paste.

The complex of the organic chemical and the chemical linker composition can also be made by simple mixing with or without heat, if the chemical linker composition is a liquid. If the chemical linker composition is a solid, the chemical linker composition must be heat above its melting point and the organic chemical mixed into the melted chemical linker composition.

The organic chemicals used in the instant invention have chemical group having dipole moments of at least about 1.5, more preferably at least one about 1.6 such as halogens affixed to a carbon atom, alcohol groups, aldehyde groups, ester groups, carboxylic acid groups, amine groups and amide groups. Typical organic chemicals contain groups with high dipole moments such as perfumes containing alcohol and aldehyde compounds, an insect repellent such as an N-lower alkyl neoalkanoamide wherein the alkyl group has 1 to 4 carbon atoms and the neodalkanoyl moiety has 7 to 14 carbon atoms, antibacterial agents such as triclosan, enzymes, proteins and allergens such as benzyl benzoate.

As used herein and in the appended claims one of the organic chemicals is a perfume which is used in its ordinary sense to refer to and include any non-water soluble fragrant substance or mixture of substances including natural (i.e., obtained by extraction of flower, herb, blossom or plant), artificial (i.e., mixture of natural oils or oil constituents) and synthetically produced substance) odoriferous substances. Typically, perfumes are complex mixtures of blends of various organic compounds such as alcohols, aldehydes, ethers, aromatic compounds and varying amounts of essential oils (e.g., terpenes) such as from 0% to 80%, usually from 10% to 70% by weight. The essential oils themselves are volatile odoriferous compounds and also serve to dissolve the other components of the perfume.

Suitable water-soluble non-soap, anionic surfactants include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble detergent.

Other suitable anionic surfactants are the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, preferably 12 to 21 carbon atoms and having the formula $RCH=CHR_1$ where R is a higher alkyl group of 6 to 23 carbons and $R_1$ is an alkyl group of 1 to 17 carbons or hydrogen to form a mixture of sultones and alkene sulfonic acids which is then treated to convert the sultones to sulfonates. Preferred olefin sulfonates contain from 14 to 16 carbon atoms in the R alkyl group and are obtained by sulfonating an a-olefin.

Other examples of suitable anionic sulfonate surfactants are the paraffin sulfonates containing 10 to 20, preferably 13 to 17, carbon atoms. Primary paraffin sulfonates are made by reacting long-chain alpha olefins and bisulfites and paraffin sulfonates having the sulfonate group distributed along the paraffin chain are shown in U.S. Pat. Nos.. 2,503,280; 2,507,088; 3,260,744; 3,372,188; and German Patent 735,096.

Examples of satisfactory anionic sulfate surfactants are the $C_8$–$C_{18}$ alkyl sulfate salts and the ethoxylated $C_8$–$C_{18}$ alkyl sulfate salts and the ethoxylated $C_8$–$C_{18}$ alkyl ether sulfate salts having the formula $R(OC_2H_4)_n\ OSO_3M$ wherein n is 1 to 12, preferably 1 to 5, and M is a metal cation selected from the group consisting of sodium, potassium, ammonium, magnesium and mono-, di- and triethanol ammonium ions. The alkyl sulfates may be obtained by sulfating the alcohols obtained by reducing glycerides of coconut oil or tallow or mixtures thereof and neutralizing the resultant product.

On the other hand, the ethoxylated alkyl ether sulfates are obtained by sulfating the condensation product of ethylene oxide with a $C_8$–$C_{18}$ alkanol and neutralizing the resultant product. The alkyl sulfates may be obtained by sulfating the alcohols obtained by reducing glycerides of coconut oil or tallow or mixtures thereof and neutralizing the resultant product. The ethoxylated alkyl ether sulfates differ from one another in the number of moles of ethylene oxide reacted with one mole of alkanol. Preferred alkyl sulfates and preferred ethoxylated alkyl ether sulfates contain 10 to 16 carbon atoms in the alkyl group.

The ethoxylated $C_8$–$C_{12}$ alkylphenyl ether sulfates containing from 2 to 6 moles of ethylene oxide in the molecule also are suitable for use in the inventive compositions. These surfactants can be prepared by reacting an alkyl phenol with 2 to 6 moles of ethylene oxide and sulfating and neutralizing the resultant ethoxylated alkylphenol.

Other suitable anionic surfactants are the $C_9$–$C_{15}$ alkyl ether polyethenoxyl carboxylates having the structural formula $R(OC_2H_4)_nOX\ CCOH$ wherein n is a number from 4 to 12, preferably 5 to 10 and X is selected from the group consisting of $CH_2\ (C(O)R_1$ and

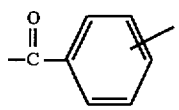

wherein $R_1$ is a $C_1$–$C_3$ alkylene group. Preferred compounds include $C_9$–$C_{99}$ alkyl ether polyethenoxy (7–9) C(O) $CH_2CH_2COOH$, $C_{13}$–$C_{15}$ alkyl ether polyethenoxy (7–9)

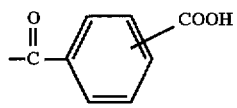

and $C_{10}$–$C_{12}$ alkyl ether polyethenoxy (5–7) $CH_2COOH$. These compounds may be prepared by considering ethylene oxide with appropriate alkanol and reacting this reaction product with chloracetic acid to make the ether carboxylic acids as shown in U.S. Pat. No. 3,741,911 or with succinic anhydride or phthalic anhydride. Obviously, these anionic surfactants will be present either in acid form or salt form depending upon the pH of the final composition, with salt forming cation being the same as for the other anionic surfactants.

Of the foregoing non-soap anionic surfactants, the preferred surfactants are the sodium or magnesium salts of the $C_8$–$C_{18}$ alkyl sulfates such as magnesium lauryl sulfate and sodium lauryl sulfate and mixtures thereof.

Generally, the proportion of the nonsoap-anionic surfactant will be in the range of 0.1% to 30%, preferably from 1% to 15%, by weight of the composition.

The instant composition can contain about 0 to about 15%, preferably about 0.25% to about 10% of an amine oxide, alkylene carbonate or zwitterionic surfactant.

The amine oxides are depicted by the formula:

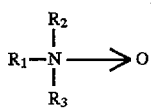

wherein $R_1$ is a $C_{10}$–$C_{16}$ a linear or branched chain alkyl group, $R_2$ is a $C_1$–$C_{16}$ linear alkyl group and $R_3$ is a $C_1$–$C_{16}$ linear alkyl group.

The zwitterionic surfactant is a water soluble betaine having the general formula:

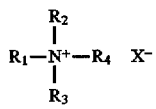

wherein $X^-$ is selected from the group consisting of $COO^-$ and $SO_3^-$ and $R_1$ is an alkyl group having 10 to about 20 carbon atoms, preferably 12 to 16 carbon atoms, or the amido radical:

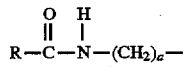

wherein R is an alkyl group having about 9 to 19 carbon atoms and a is the integer 1 to 4: $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N,N-dimethyl-ammonia) acetate, coco dimethyl betaine or 2-(N-coco N,N-dimethylammonia) acetate, myristyl dimethyl betaine, palmityl dimethyl betaine, lauryl dimethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine. Three preferred betaine surfactants are Genagen CAB and Rewoteric AMB 13 and Golmschmidt Betaine L7.

The alkylene carbonate surfactant is depicted by the following formula:

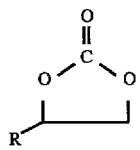

wherein R is an alkyl group having about 4 to about 14 carbon atoms, more preferably about 6 to about 10 carbon atoms.

The instant compositions contain about 0.5 wt. % to about 10 wt. %, more preferably about 1 wt. % to about 7.0 wt. % of a chemical linker composition which is an ethoxylated glycerol type compound and, optionally, a compound which is selected from the group consisting of a carboxylic acid having 4 to 6 carbon atoms and a Lewis base, neutral polymer which is soluble in water and has either a nitrogen or oxygen atom with a pair of free electrons such that the Lewis base, neutral polymer can electronically associate with the anionic surfactant and the organic chemical having a dipole moment of at least about 1.5 such as an enzyme, protein, allergen agent, a perfume or an antimicrobial agent such as triclosan or an insect repellent such as MNDA wherein the chemical linker composition is deposited and anchored onto the surface of the surface being treated thereby holding the organic chemical in close proximity to the surface thereby ensuring that the properties being parted by the organic chemical last longer. The chemical linker composition can also link with the anionic surfactant to hold the anionic surfactant in close proximity to the surface being cleaned.

The Lewis base, neutral polymers are selected from the group consisting of a polyvinyl pyrrolidone polymer and a polyethylene glycol and mixtures thereof.

The instant compositions contain about 0.1 to 20 wt. %, more preferably about 0.5 to 15 wt. % of the chemical linker composition which comprises an ethoxylated glycerol type compound and/or, optionally, a carboxylic acid and/or a Lewis base. The concentration of the ethoxylated glycerol type composition in the instant compositions is about 0.1 to about 20 wt. %, more preferably about 0.5 to about 15 wt. %. The concentration of the carboxylic acid and/or the Lewis base is 0 to about 15 wt. %, more preferably 0.25 to 10 wt. %.

The ethoxylated polyhydric (glycerol) type compound which is a mixture of a fully esterified ethoxylated polyhydric alcohol, a partially esterified ethoxylated polyhydric alcohol and a nonesterified ethoxylated polyhydric alcohol, wherein the preferred polyhydric alcohol is glycerol, and the compound is:

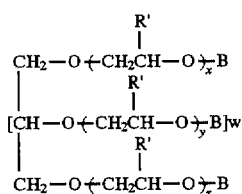

Formula (I)

and

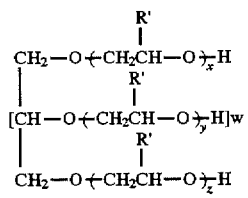

Formula (II)

wherein w equals one to four, most preferably one, and B is selected from the group consisting of hydrogen or a group represented by:

wherein R is selected from the group consisting of alkyl group having 6 to 22 carbon atoms, more preferably 11 to 15 carbon atoms and alkenyl groups having 6 to 22 carbon atoms, more preferably 11 to 15 carbon atoms, wherein a hydrogenated tallow alkyl chain or a coco alkyl chain is most preferred, wherein at least one of the B groups is represented by said

and R' is selected from the group consisting of hydrogen and methyl groups; x, y and z have a value between 0 and 60, more preferably 0 to 40, provided that (x+y+z) equals 2 to 100, preferably 4 to 24 and most preferably 4 to 19, wherein in Formula (I) the weight ratio of monoester/diester/triester is 40 to 90/5 to 35/1 to 20, more preferably 50 to 90/9 to 32/1 to 12, wherein the weight ratio of Formula (I) to Formula (II) is a value between 3 to 0.02, preferably 3 to 0.1, most preferably 1.5 to 0.2, wherein it is most preferred that there is more of Formula (11) than Formula (I) in the mixture that forms the compound.

The ethoxylated glycerol type compound used in the instant composition is manufactured by the Kao Corporation and sold under the trade name Levenol such as Levenol F-200 which has an average EO of 6 and a molar ratio of coco fatty acid to glycerol of 0.55 or Levenol V501/2 which has an average EO of 17 and a molar ratio of tallow fatty acid to glycerol of 1.0. It is preferred that the molar ratio of the fatty acid to glycerol is less than 1.7, more preferably less than 1.5 and most preferably less than 1.0. The ethoxylated glycerol type compound has a molecular weight of 400 to 1600, and a pH (50 grams/liter of water) of 5–7. The Levenol compounds are substantially non irritant to human skin and have a primary biodegradability higher than 90% as measured by the Wickbold method Bias-7d.

Two examples of the Levenol compounds are Levenol V-501/2 which has 17 ethoxylated groups and is derived from tallow fatty acid with a fatty acid to glycerol ratio of 1.0 and a molecular weight of 1465 and Levenol F-200 has 6 ethoxylated groups and is derived from coco fatty acid with a fatty acid to glycerol ratio of 0.55. Both Levenol F-200 and Levenol V-501/2 are composed of a mixture of Formula (I) and Formula (II). The Levenol compounds has ecoxity values of algae growth inhibition>100 mg/liter; acute toxicity for Daphniae>100 mg/liter and acute fish toxicity>100 mg/liter. The Levenol compounds have a ready biodegradability higher than 60% which is the minimum required value according to OECD 301B measurement to be acceptably biodegradable.

The polyvinyl pyrrolidone polymer is depicted by the formula:

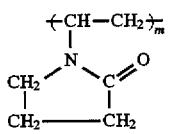

wherein m is about 20 to about 350 more preferably about 70 to about 110.

The polyethylene glycol is depicted by the formula:

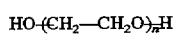

wherein n is about 8 to about 225, more preferably about 10 to about 100,000, wherein one preferred polyethylene glycerol is PEG1000 which is a polyethylene glycol having a molecular weight of about 1000.

The following examples illustrate the complexes of additives and chemical linker composition and liquid cleaning compositions containing complexes of the chemical linker composition with the organic chemical and/or surfactant invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE 1

The following complexes of chemical additive and chemical linker were made:

Tests were run with a microcalorimeter CALVET. A cell contains 0.5 g of the chemical additive and 0.5 g of a chemical linker such as polyethylene glycol in two separated parts. A semi circular cup disposed with in the cell allows the mixing of the two components in the cell. The heat flow generated by the mixing is measured. If the components interact together, their mixing releases heat. The table hereafter gives the components of the mixture, the time and the microwatt value to the maximum of the exothermic peak.

|  | A | B | C | D | E | F | G | H | I | J |
|---|---|---|---|---|---|---|---|---|---|---|
| Chemical additives |  |  |  |  |  |  |  |  |  |  |
| Quat ester | 0.5 |  |  |  |  |  |  |  |  |  |
| Benzyl benzoate |  | 0.5 |  |  |  |  |  |  |  |  |
| Dihydromyrcenol - Perfume |  |  | 0.5 |  |  |  |  |  |  |  |

-continued

|  | A | B | C | D | E | F | G | H | I | J |
|---|---|---|---|---|---|---|---|---|---|---|
| Aldehyde C9 - Perfume |  |  |  | 0.5 |  |  |  |  | 0.5 |  |
| Triclosan |  |  |  |  | 0.5 |  |  |  |  |  |
| MNDA |  |  |  |  |  | 0.5 |  |  |  | 1.5 |
| n-dimethyl para-amine octyl benzoate |  |  |  |  |  |  | 0.5 |  |  |  |
| BSA - Protein |  |  |  |  |  |  |  | 0.5 |  |  |
| PEG 200 |  |  |  | 0.5 |  |  |  |  |  |  |
| PEG 600 | 0.5 | 0.5 |  |  | 0.5 |  |  | 0.5 |  |  |
| PEG 6000 |  |  | 0.5 |  |  | 0.5 | 0.5 |  |  |  |
| Exothermic reaction |  |  |  |  |  |  |  |  |  |  |
| Microwatte to exothermic energy peak | 1070 | 3240 | 115 | 55500 | 327 | 171 | 98 | 700 | 39700 | 1934 |
| Time (seconds) to energy peak | 80 | 130 | 30 | 40 | 120 | 130 | 140 | 820 | 380 | 670 |
| Levenol F-200 |  |  |  |  |  |  |  |  | 0.5 |  |
| Isobutyric Acid |  |  |  |  |  |  |  |  |  | 0.3 |

EXAMPLE 2

The following compositions were made by simple mixing at 25° C.

|  | A | B | C | D | E | F |
|---|---|---|---|---|---|---|
| Sodium lauryl sulfate (Empicol LX-28 Hoechst) | 21.43 | 21.43 | 21.43 | 21.43 | 21.43 | 21.43 |
| Lauryl alkyldimethyl betaine (Genaga LAB-Hoechst) | 6.67 | 6.67 | 6.67 | 6.67 | 6.67 | 6.67 |
| Formalin | 0.1 | 0.1 | 0.1 | 0.1 | 0.1 | 0.1 |
| PEG. MW 400 |  | 1.0 |  | 1.0 |  | 1.0 |
| Limonene fragrance | 0.1 | 0.1 |  |  |  |  |
| D-citronellol fragrance |  |  | 0.31 | 0.30 |  |  |
| Aubepine fragrance |  |  |  |  | 0.33 | 0.32 |
| Water |  | Bal. | Bal. | Bal. | Bal. | Bal. |
| Static headscape/Gp measurements | 1,366,797 | 1,538,430 | 44,086 | 46,335 | 18,171 | 18,832 |

Static headspace/GC measurements were made—5 gm samples of formulas (A–F) were placed into 22 ml. headspace vials. The samples were analyzed on a Perkin-Elmer HS-100 attached to a Signma GC. Samples were thermostated at 60° C. for 60 minutes and following transfer (transfer line temperature: 140° C.) to the GC, the volatiles were separated on a Supelcowax (30M×0.32 mm, 0.25 m coating) column. The GO was equipped with an FID (detector temperature: 225° C.), helium was used as the carrier gas (7.2 ml/min.), and the oven temperature program began with an initial oven temperature of 50° C. for 2 min., then ramped to 175° C. at 6° C./min. and held for 2 minutes. All peaks were automatically integrated by the Turbochrom 3 data acquisition and analysis software, version 3.3, loaded on a Gateway 386/33 computer.

What is claimed is:

1. A method for improving the retention time of an organic chemical which comprises the steps of:

(a) adding said organic chemical having a chemical group having a dipole moment of at least about 1.5 to a chemical linker composition which is an ethoxylated glycerol type compound and a compound selected from the group consisting of a polyvinyl pyrrolidone polymer and a polyethylene glycol having a molecular weight of about 600 to about 10,000 to form a complex, wherein the molar ratio of the chemical linker composition to the organic chemical is about 4:1 to 1:4 and applying the complex of organic chemical and chemical linker composition onto a surface which is being treated.

2. A composition comprising:

(a) 0.1% to 10% of an organic chemical having a chemical group having a dipole moment of at least about 1.5;

(b) 0 to 30% of at least one anionic surfactant;

(c) 0 to 15% of a surfactant selected from the group consisting of alkylene carbonates, zwitterionics and amine oxides and mixtures thereof;

(d) 0.1% to 20% of an ethoxylated glycerol type compound;

(e) 0.25% to 10% of a compound selected from the group consisting of polyethylene glycol, and polyvinyl pyrrolidone polymer; and (f) 15% to 99.8% of water.

3. A composition according to claim 2 wherein said ethoxylated glycerol type compound is a mixture of:

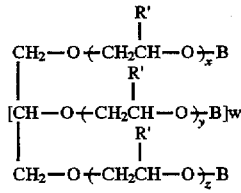

(I)

and

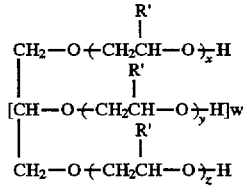

(II)

wherein w equals one to four, and B is selected from the group consisting of hydrogen or a group represented by:

wherein R is selected from the group consisting of alkyl group having 6 to 22 carbon atoms, and alkenyl groups having 6 to 22 carbon atoms, wherein at least one of the B groups is represented by said

R' is selected from the group consisting of hydrogen and methyl groups; x, y and z have a value between 0 and 60, provided that (x+y+z) equals 2 to 100, wherein in Formula (I) the weight ratio of monoester/diester/triester is 40 to 90/5 to 35/1 to 20, wherein the weight ratio of Formula (I) and Formula (II) is a value between 3 to 0.02.

4. A composition according to claim 3, wherein the surfactant selected from the group consisting of alkylene carbonates, zwitterionics and amine oxides and mixtures thereof is at a concentration of about 0.25 wt. % to 10 wt. %.

5. A composition comprising:

(a) 0.1% to 10% of an organic chemical having a chemical group having a dipole moment of at least about 1.5;

(b) 0 to 30% of at least one anionic surfactant;

(c) 0.25% to 10% of a surfactant selected from the group consisting of alkylene carbonates, zwitterionics and amine oxides and mixtures thereof;

(d) 0.1% to 20% of an ethoxylated glycerol type compound;

(e) 0.25% to 10% of a carboxylic acid having about 4 to 6 carbon atoms; and (f) 15% to 99.8% of water.

6. A composition according to claim 5 wherein said ethoxylated glycerol type compound is a mixture of:

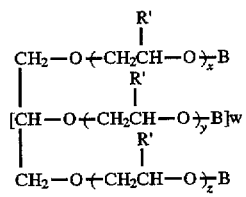

and

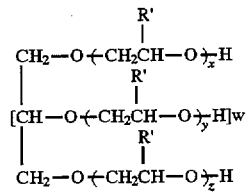

wherein w equals one to four, and B is selected from the group consisting of hydrogen or a group represented by:

wherein R is selected from the group consisting of alkyl group having 6 to 22 carbon atoms, and alkenyl groups having 6 to 22 carbon atoms, wherein at least one of the B groups is represented by said

R' is selected from the group consisting of hydrogen and methyl groups; x, y and z have a value between 0 and 60, provided that (x+y+z) equals 2 to 100, wherein in Formula (I) the weight ratio of monoester/diester/triester is 40 to 90/5 to 35/1 to 20, wherein the weight ration of Formula (I) and Formula (II) is a value between 3 to 0.02.

* * * * *